United States Patent [19]
Baccaro

[11] Patent Number: 6,010,517
[45] Date of Patent: *Jan. 4, 2000

[54] DEVICE FOR OCCLUDING ABNORMAL VESSEL COMMUNICATIONS

[76] Inventor: Jorge Alberto Baccaro, Chile 1685, Corrientes, Pcia. de Corrientes, Argentina

[ * ] Notice: This patent issued on a continued prosecution application filed under 37 CFR 1.53(d), and is subject to the twenty year patent term provisions of 35 U.S.C. 154(a)(2).

[21] Appl. No.: 08/832,207

[22] Filed: Apr. 8, 1997

[30] Foreign Application Priority Data

Apr. 10, 1996 [AR] Argentina .................................. 336114

[51] Int. Cl.$^7$ .................................................. A61B 17/08
[52] U.S. Cl. .......................... 606/151; 606/157; 606/158; 606/213
[58] Field of Search ..................................... 606/151, 157, 606/158, 213, 214, 215, 216

[56] References Cited

U.S. PATENT DOCUMENTS

| | | | |
|---|---|---|---|
| 5,192,301 | 3/1993 | Kamiya et al. | 606/213 |
| 5,454,833 | 10/1995 | Boussignac et al. | 606/213 |
| 5,522,822 | 6/1996 | Phelps et al. | 606/151 |
| 5,626,599 | 5/1997 | Bourne et al. | 606/194 |
| 5,634,936 | 6/1997 | Linden et al. | 606/213 |

*Primary Examiner*—Michael Buiz
*Assistant Examiner*—Tina T. D. Pham
*Attorney, Agent, or Firm*—Bachman & LaPointe, P.C.

[57] ABSTRACT

A device for occluding abnormal vessel communications is of the type comprised by a wire which, being pre-formed as a means of endo-luminal blocking and being stretchable in the direction of its longitudinal axis, has heat-sensitive resilient memory; said wire, which is to be introduced into an abnormal vessel communication, such as that produced between arteries and veins, or between systemic arterial circulation and pulmonary circulation, is characterized in that the wire is shaped as a conical spiral, the apex of which is followed by a terminal portion of the same wire, bent as a hook; such that the loops of said wire define portions of different diameter, which may be adapted to the vessel gap or passage, while the end as a hook is a means for anchoring the occluding device, emerging through the smaller end of the lumen.

6 Claims, 1 Drawing Sheet

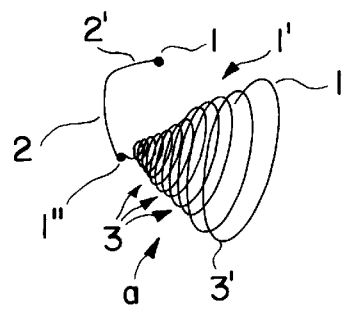
FIG. 1
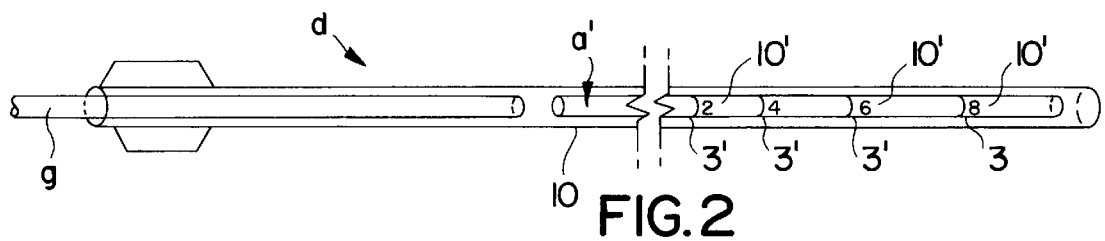
FIG. 2
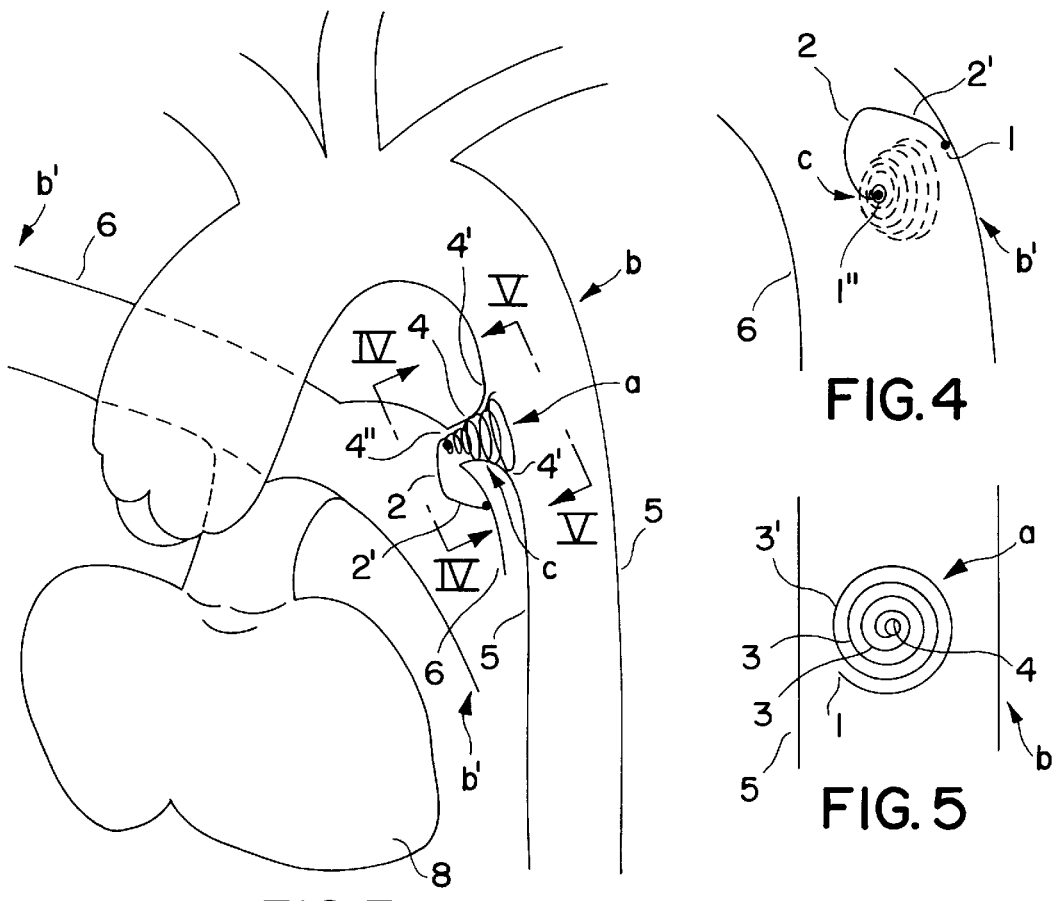
FIG. 3
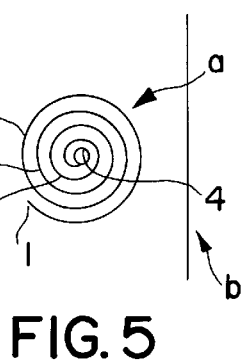
FIG. 4
FIG. 5

DEVICE FOR OCCLUDING ABNORMAL VESSEL COMMUNICATIONS

FIELD OF THE INVENTION

The instant invention relates to a device for occluding abnormal vessel communications, and, in general, comprises a wire shaped as a conical spiral, which is perfectly adaptable to the vessel lumen thus allowing the formation of a self-occluding thrombus.

BACKGROUND OF THE INVENTION-PRIOR ART

During fetus life there are vessel communications which normally disappear upon reaching adult life. These communications are called "ductus", among which arterial ductus, between the pulmonary artery and the aorta; venous ductus communicating the left umbilical vein to the heart right venous sinus; Cuvier ductus comprised of pairs of common cardinal veins; etc, may be mentioned.

When an individual reaches adult life and such ductus or fetal conduits persist, their closure is required by means of a surgery requiring thorax aperture.

Alternatively, during the last years intra-vascular treatments have been widely known in the medicine field. These are characterized by being carried out through the interior of the vessel lumen, instead of using surgery, i.e. instead of cutting tissues to reach the damaged artery or vein.

These intra-vascular treatments are effected within the vessel lumen, using different means and serving several purposes among which, the following may be mentioned: producing dilation of the artery or vein, dissolving thrombi therein, coating vessel inner walls with a prosthesis, recover the normal lumen of an artery dilated due to aneurysm and closing abnormal communications of these vessels, among others.

In case of abnormal vascular communications, the means used comprise occluding devices having shapes similar to plugs, umbrellas, springs, etc.

Some of the known devices used at present have the disadvantage that their size varies according to the ductus in which it will be used. Therefore, when the ductus is large, the artery access section constitutes a limitation.

Other devices used are Ivalon plugs and Rashkin umbrella. Particularly, in the latter, efforts have been made to solve its disadvantages by means of a device comprising a polyurethane double-umbrella. This is a device having at its ends corresponding sets of radially projected arms, similar to the rods of two umbrellas located one at each side of the ductus passage.

Such device, which is introduced by means of a catheter and pushing means and with the arms of both umbrellas folded in order to reach the operation region, is difficult to locate and unfold precisely. As a result, a complete occlusion is not attained in at least 15% of patients.

Further, the risk is run that, if one of the umbrellas slips off, it causes embolia at the lung. Further disadvantages is that such device is suitable for ductus up to 8 mm and it is expensive.

Other occluding devices are known comprised by a cylindrical spiral, having loops of equal diameter and a determined length. There are two types: Gianturco and Jackson. The latter has connecting means allowing its control and further it has fibers which, similar to small hairs, facilitate the formation of the occluding clot around the device. The device should be stretched at the intermediate region, due to which it adapts to the ductus passage, while the ends retaining their cylindrical spiral shape accommodate to the ends of the passage.

This kind of device is cheap and has reduced section, but limitation in use is of 3 mm; therefore it could not be employed for larger ductus which, on the other hand, are the majority.

SUMMARY OF THE INVENTION

The instant invention overcomes all limitations and disadvantages of known devices. In fact, the occluding device of the instant invention is made from a wire shaped as a conical spiral. The apex of this spiral is followed by a end portion of the same wire, bent as a hook; such that the loops of said wire define portions of different diameter, which may be adapted to the vessel lumen. Thus, the terminal hook constitutes a means anchored to the walls of one of the vessels, located at a zone opposite to that of the larger diameter loop which, in turn, bears on the walls of the other vessel.

Due to the pressure differences existing between vessel conduits with abnormal communications or ductus, the passage thereof has a frusto-conical shape to which the conical device of the invention is perfectly adapted.

On the other hand, the occluding device of the invention is comprised by a wire made of a material such as nytinol having heat-sensitive resilient memory, due to this reason it is pre-formed as a conical spiral, being then stretched in the direction of its longitudinal axis.

With this stretched shape, it may be applied by the same catheters as those used for diagnosis, which have a very small diameter, therefore they adapt to thin vessels such as those of low weight children.

Once the device is located, the heat-sensitive resilient memory allows recovery of its shape to a conical spiral. Thus, this device is equally suitable for ductus as well as for cases of traumatic fistula and congenital malformation.

The invention also provides a cartridge for applying the device within which the wire is stretched. Once the dimensions of the abnormal vessel communication passage are determined, the cartridge containing the occluding device is cut to the correct size using as a guide an indexed scale indicating the position of each loop. In this way loops are eliminated and the device size is defined; therefore devices of different sizes are not required.

Finally, the device of the invention may be coated with a bio-compatible and thrombogenic material, such as tungsten,, being this very important since the occlusion is carried out by a thrombus formed on the occluding device. Also, it should be added that production costs of this occluding device are comparatively low.

BRIEF DESCRIPTION OF THE DRAWINGS

FIG. 1 is a perspective view showing the general structure of the occluding device. The wire shaped as a conical spiral and, from the apex, the end portion shaped as a hook are also shown.

FIG. 2 is a side view of the device for applying the device. The scale indicating the position of each loop, determining the cutting points for removing excess loops is also shown.

FIG. 3 is a scheme showing the abnormal communication or ductus existing between the aorta and the lung artery. The occluding device is located within the lumen, with its end portion anchored to the walls of the second vessel conduit.

FIG. 4 is a longitudinal section of the second vascular conduit (lung artery) from the plane along line IV—IV in FIG. 3. The smaller end of the ductus lumen is shown, and also, ascending, the end portion of the device.

FIG. 5 is a longitudinal section of the first vascular conduit (aorta) from a plane along line V—V in FIG. 3. The larger end of the ductus lumen is shown, and also, in front of it, the conical spiral of the device.

In the figures, the same reference numerals indicate the same or corresponding parts, and assemblies of several elements have been designated with letters.

LIST OF MAIN REFERENCE (a) conical occluding device
(a') unformed occluding device
(b) first vascular conduit [aorta of systemic arterial circulation]
(b') second vascular conduit [lung artery of pulmonary arterial circulation]
(c) abnormal vessel communication or ductus.
(d) cartridge for applying the device.
(1) wire forming (a)
(1') conical spiral
(1") apex of (a)
(2) end portion
(2') bent of (2) in the shape of a hook
(3) loops of (1)
(3') larger diameter or base loop
(4) communication lumen (c)
(4') larger end of (4)
(4") smaller end of (4)
(5) walls of the first vascular conduit (b)
(6) walls of the second vascular conduit (b')
(7) right auricle
(8) right ventricle
(9) pusher
(10) walls of cartridge (d)
(10') numerical scale for indicating loops (3)

MAIN OBJECT OF THE INVENTION

The device (a) for occluding abnormal vessel communications (c) is of the type comprised by a wire (1) which, being pre-shaped as a means of endo-luminal blocking and being stretchable in the direction of its longitudinal axis, has heat sensitive resilient memory; said wire (1), which is to be introduced into an abnormal vessel communication (c), such as that produced between arteries and veins, or between systemic arterial circulation (b) and pulmonary circulation (b'), is characterized in that the wire is shaped as a conical spiral, the apex of which (1') is followed by a terminal portion (2) of the same wire (1), bent as a hook (2') such that the loops (3) of said wire (1) define portions of different diameter, which may be adapted to the vessel lumen (4), while the end (2) as a hook (2') is a means for anchoring the occluding device (a), located at the region opposed to that of the larger diameter loop (3').

DETAILED DESCRIPTION OF THE INVENTION

The instant invention relates to a device for occluding abnormal vessel communications.

It is a device (a) for being introduced, as blocking means, into the lumen (4) of an abnormal vessel communication or ductus (c) existing between corresponding vascular conduits (b) and (b'), such as that produced between arteries and veins, or between systemic arterial circulation and pulmonary circulation.

The occluding device (a) is comprised by a wire (1) which, being preformed as an endo-luminal blocking means and being stretchable in the direction of its longitudinal axis, has heat-sensitive resilient memory.

More particularly, the wire (1) forming the occluding device (a) is shaped as a conical spiral (1'). In this way, the wire (1) forms loops (3) defining different diameter portions, beginning with a larger diameter loop (3') at the corresponding end of the conical base and closing, at the opposite end, into an apex (1"). From apex (1") the wire (1) is followed by a terminal portion (2) having a bent shaped as a hook (2'). [See FIG. 1]

This terminal portion (2) following the apex (1") of the conical spiral (1'), may be bent to 90° having a second bent affording the mentioned shape of open hook (2').

Considering the above, the loops (3) of different diameter may be adapted to the vessel lumen (4), while the terminal portion (2) as a hook (2') constitutes a means for anchoring the occluding device.

To be positioned into the abnormal communication or ductus (c) to be occluded, the occluding device (a) has an application cartridge (d) comprised by a tube within which the wire (1) pre-formed and stretched in its own longitudinal direction is located. On the walls (10) of the cartridge (d) there is an alpha-numerical scale (10') each division of which indicates the position corresponding to one of the loops (3) of the conical spiral (1'). [As may be seen in FIG. 2].

OPERATION

Abnormal vessel communications (c) are produced between vascular conduits (b) and (b') of arteries and veins, on one hand, or pertain to systemic and pulmonary arterial circulation on the other.

In the instant embodiment, the first vascular conduit (b) is comprised by the aorta (b) pertaining to systemic arterial circulation, while the second vascular conduit (b') is constituted by the lung artery (b') corresponding to pulmonary arterial circulation. [See FIG. 3].

As may be seen in FIG. 3, between both vessel conduits (b) and (b') there is an abnormal vessel communication or ductus (c) comprising an abnormal vessel lumen (4). Due to the higher circulating pressure existing into the first conduit (b) with respect to the second (b'), the vessel lumen (4) has frusto-conical shape. In this way, the end (4') of lumen (4) corresponding to the first vessel conduit (b), appears to be larger, while end (4") of lumen (4) corresponding to the second conduit (b') is smaller.

Further, and as mentioned before, the occluding device is formed by a wire (1) having heat-sensitive resilient memory, thus being pre-formed as a conical spiral (1"), being then stretchable in the direction of its longitudinal axis [See FIG. 1].

Once the size of lumen (4) of the abnormal vessel communication (c) is determined, the cartridge (d) is cut to the required length, the scale (10') serving as a guide indicating the position of each loop (3). [See FIG. 2].

Under these conditions and by means of a pusher (9) the cartridge (d) reaches the operating region, wherein the occluding device is released (a), said device, due to its heat-sensitive resilient memory, acquiring its shape of conical spiral (1'). Since loops (3) define portions of different diameter, the device (a) is adapted to the frusto-conical passage (4) of the abnormal communication (c), as from the larger diameter or base loop (3') at the larger end (4') of the lumen (4), against the walls (5) of the first vascular conduit (b) [see FIGS. 3 and 5].

In turn, apex (1") of device (a) projects through the smaller end (4") of said lumen (4), the end portion (2) shaped as a hook (2') being an anchoring means against walls (6) of the second vascular conduit (b'). [See FIG. 4].

Obviously, when practicing the invention, many modifications may be introduced without departing from the basic principles thereof, which are only supported by the appended claims.

I claim:

1. A vasoocclusive device adapter to be introduced into and anchored in a vascular lumen comprises an elongated, conical shaped, spiral coil extending along a longitudinal axis from one end of a first diameter loop to another end of a second diameter loop which is smaller than the first diameter loop, said second diameter loop at the other end of the elongated, conical shaped, spiral coil ends in an apex and has extending from the apex hook means for anchoring the device in the vascular lumen said hook means extending radially beyond said second diameter loop.

2. A device as claimed in claim 1, wherein the spiral coil is formed of a heat-sensitive resilient memory wire.

3. A device as claimed in claim 2, wherein the coil is coated by a biocompatible and thrombogenic material.

4. A device as claimed in claim 3, wherein the wire is coated with tungsten.

5. A device as claimed in claim 2, wherein the hook means is comprised by a terminal portion of said wire, said portion being bent to about a 90° angle with respect to the longitudinal axis and which terminates in a second intermediate bent portion in the form of an open hook.

6. An apparatus for introducing a vasoocclusive device in a vascular lumen comprises, in combination, a vasoocclusive device having an elongated, conical shaped, spiral coil extending along a longitudinal axis from one end of a first diameter loop to an other end of a second diameter loop which is smaller than the first diameter loop, said second diameter loop at the other end of the elongated, conical shaped, spiral coil ends in an apex and has extending from the apex hook means for anchoring the device in the vascular lumen said hook means extending radially beyond said second diameter loop, and a cartridge comprises a tubular body for receiving said vasoocclusive device, said tubular body having an indexed scale indicating the position of each loop of the vasoocclusive device, and a pusher associate with said tubular body and said occlusive device for introducing said occlusive device into the vascular lumen.

* * * * *